(12) United States Patent
Seeberger et al.

(10) Patent No.: US 9,694,187 B2
(45) Date of Patent: Jul. 4, 2017

(54) IMPLANTABLE MEDICAL DEVICES AND METHODS INCLUDING POST-PROCEDURAL SYSTEM DIAGNOSTICS

(71) Applicant: CARDIAC PACEMAKERS, INC., St. Paul, MN (US)

(72) Inventors: Michael Sheehan Seeberger, Afton, MN (US); Scott R. Vanderlinde, Plymouth, MN (US); Wyatt Keith Stahl, Little Canada, MN (US); Imelda Wang, Edina, MN (US); Scott H. Thomas, Apple Valley, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 14/800,133

(22) Filed: Jul. 15, 2015

(65) Prior Publication Data

US 2016/0015986 A1    Jan. 21, 2016

Related U.S. Application Data

(60) Provisional application No. 62/025,313, filed on Jul. 16, 2014.

(51) Int. Cl.
*A61N 1/37* (2006.01)
*A61N 1/372* (2006.01)

(52) U.S. Cl.
CPC .......... *A61N 1/3706* (2013.01); *A61N 1/371* (2013.01); *A61N 1/3718* (2013.01); *A61N 1/37247* (2013.01)

(58) Field of Classification Search
CPC ................ A61N 1/08; A61N 2001/083; A61N 2001/086; A61N 2001/37294
(Continued)

(56) References Cited

U.S. PATENT DOCUMENTS

| | | |
|---|---|---|
| 3,979,005 A | 9/1976 | Robinson et al. |
| 4,562,841 A | 1/1986 | Brockway et al. |
| | (Continued) | |

FOREIGN PATENT DOCUMENTS

| | | |
|---|---|---|
| DE | 19524680 | 1/1997 |
| FR | 1591601 | 5/1970 |
| | (Continued) | |

OTHER PUBLICATIONS

Choudhuri, M.D., Indrajit et al., "Feasibility of Early Discharge after Implantable Cardioverter-Defibrillator Procedures," 'Accepted Article', doi: 10.1111/j.1540-8167.2012.02367.x, 2012 (20 pages).

(Continued)

*Primary Examiner* — Paula J Stice
(74) *Attorney, Agent, or Firm* — Pauly, DeVries Smith & Deffner, L.L.C.

(57) ABSTRACT

Aspects herein include an implantable medical device, such as an implantable cardiac rhythm management device. The implantable medical device can include a housing, control circuitry disposed within the housing, and telemetry circuitry in electrical communication with the control circuitry. The control circuitry can be configured to execute a post-procedural system check procedure after the expiration of a preselected first time period. The first time period can be greater than or equal to 0.5 hours and less than or equal to 48 hours. In various aspects, the post-procedural system check procedure can include measuring diagnostic properties for one or more electrodes of an electrical stimulation lead attached to the implantable medical device. The first time period can begin to elapse after detection of a triggering event or a command by a system operator.

10 Claims, 8 Drawing Sheets

(58) Field of Classification Search
USPC .......................................................... 607/119
See application file for complete search history.

(56) References Cited

U.S. PATENT DOCUMENTS

| | | | |
|---|---|---|---|
| 5,534,018 A | 7/1996 | Wahlstrand et al. | |
| 5,755,742 A | 5/1998 | Schuelke et al. | |
| 6,101,417 A * | 8/2000 | Vogel | A61N 1/37217 607/30 |
| 6,778,855 B2 | 8/2004 | Eberle et al. | |
| 6,978,182 B2 | 12/2005 | Mazar et al. | |
| 8,060,205 B2 | 11/2011 | Conley et al. | |
| 8,725,261 B2 | 5/2014 | Enrooth et al. | |
| 2008/0262561 A1 | 10/2008 | Catto et al. | |
| 2009/0157146 A1* | 6/2009 | Linder | A61N 1/37217 607/60 |
| 2009/0321045 A1 | 12/2009 | Hernon et al. | |
| 2012/0283795 A1* | 11/2012 | Stancer | A61N 1/3688 607/11 |
| 2013/0058042 A1 | 3/2013 | Salamon et al. | |

FOREIGN PATENT DOCUMENTS

| | | |
|---|---|---|
| GB | 1358073 | 6/1974 |
| WO | 0114003 | 3/2001 |
| WO | 03002198 | 1/2003 |
| WO | 2012148154 | 10/2012 |
| WO | 2016011243 | 1/2016 |

OTHER PUBLICATIONS

"Contak Renewal 4 RF System Guide," Guidant Corporation, 2008 (337 pages).
"Implantable Cardioverter Defibrillator (ICD)," Implantation/Coding Overview, Boston Scientific, 2007 (8 pages).
"Therapeutic Radiation and Implantable Device Systems," Boston Scientific, 002-1675, Rev. B. (2012) p. 1-6.
"Invitation to Pay Additional Fees," for PCT/US2015/040732 mailed Nov. 10, 2015 (7 pages).
"International Preliminary Report on Patentability," for PCT Application No. PCT/US2015/040732 mailed Jan. 26, 2017 (15 pages).

* cited by examiner

IMPLANTABLE MEDICAL DEVICES AND METHODS INCLUDING POST-PROCEDURAL SYSTEM DIAGNOSTICS

This application claims the benefit of U.S. Provisional Application No. 62/025,313 filed Jul. 16, 2014, the contents of which are herein incorporated by reference.

FIELD

Aspects herein relate to an implantable medical device and related methods. More specifically, aspects herein relate to an implantable medical device configured to execute a post-procedural diagnostic procedure and related methods.

BACKGROUND

Patients commonly have medical devices implanted to aid in the functioning of an organ of the body, such as the heart. After a procedure to implant a medical device, a clinician can run tests to determine if the device is operating correctly. By way of example, in the context of a device that delivers electrical stimulation, the clinician can verify that the implanted device and associated stimulation leads are operating as expected prior to the patient being discharged from the healthcare facility.

SUMMARY

In an aspect, an implantable cardiac rhythm management device is included having a housing, control circuitry disposed within the housing, and telemetry circuitry in electrical communication with the control circuitry. The control circuitry can be configured to execute a post-procedural system check procedure after the expiration of a preselected first time period. The first time period can be greater than or equal to 0.5 hours and less than or equal to 48 hours. The post-procedural system check procedure can include measuring diagnostic properties for one or more of a plurality of electrodes of an electrical stimulation lead attached to the implantable cardiac rhythm management device. The first time period can begin to elapse after detection of a triggering event or a command by a system operator.

In addition, or alternatively, the triggering event can include an implant-related event.

In addition, or alternatively, the implant-related event can be the connection of the electrical stimulation lead to the implantable cardiac rhythm management device and/or exiting of the implantable cardiac rhythm management device out of a storage mode.

In addition, or alternatively, the triggering event can include the detection of an MRI time varying magnetic field.

In addition, or alternatively, the triggering event can include the initiation of a magnet pacing mode.

In addition, or alternatively, the diagnostic properties can include at least one selected from the group consisting of an impedance test, an intrinsic amplitude test, and a pacing threshold test.

In addition, or alternatively, the control circuitry can be configured to send an indication of the current status and/or data from of the post-procedural system check if the implantable cardiac rhythm management device is interrogated during the post-procedural system check.

In addition, or alternatively, the control circuitry can be configured to report the results of the post-procedural system check procedure via the telemetry circuitry to an external device at the next communication request.

In addition, or alternatively, the external device can be in the proximity of the patient in which the implantable cardiac rhythm management device is implanted, but is remote from a care provider.

In addition, or alternatively, the first time period can be greater than or equal to 2 hours and less than or equal to 24 hours.

In addition, or alternatively, a default length of the first time period can be stored by the control circuitry prior to the device exiting a storage mode.

In addition, or alternatively, the control circuitry can be configured to accept input from a system operator specifying a desired time for the post-procedural system check results to be available.

In addition, or alternatively, the control circuitry calculates the length of the first time period time based on the input, wherein the length of the first time period is less than the amount of time specified by the operator.

In an aspect, a medical device system is included having an implantable cardiac rhythm management device and an external medical device in wireless communication with the implantable cardiac rhythm management device. The control circuitry of the external medical device can be configured to display information through the display device regarding the results of a previously executed post-procedural system check procedure. In some embodiments, the control circuitry of the external medical device can be configured to print information regarding the results of a previously executed post-procedural system check procedure through a printing device. The implantable cardiac rhythm management device can include a housing, control circuitry disposed within the housing, and telemetry circuitry in electrical communication with the control circuitry. The control circuitry can be configured to execute a post-procedural system check procedure after the expiration of a preselected first time period. The first time period can be greater than or equal to 0.5 hours and less than or equal to 48 hours. The post-procedural system check procedure can include measuring diagnostic properties for one or more of a plurality of electrodes of an electrical stimulation lead attached to the implantable cardiac rhythm management device. The first time period can begin to elapse after detection of a triggering event or a command by a system operator. The external medical can include a housing, control circuitry disposed within the housing, telemetry circuitry in electrical communication with the control circuitry, an output device comprising at least one of a display device or a printing device in electronic communication with the control circuitry, and an operator input device operatively coupled to the housing (directly coupled or separate).

In addition, or alternatively, the control circuitry of the external medical device can be configured to display information through the display device informing an external medical device operator that a post-procedural system check is in process, if execution of an attempted post-procedural system check procedure has not terminated.

In addition, or alternatively, the control circuitry of the external medical device can be configured to display one or more fields regarding recent impedance values measured, wherein the fields are populated with information from a previously executed post-procedural system check or an automatic daily lead test, whichever is more recent.

In addition, or alternatively, the control circuitry of the external medical device can be configured to accept input from a system operator through the operator input device regarding a desired time for the post-procedural system check results to be available; wherein the external medical device displays information to the system operator through the display device regarding an acceptable range of the operator input, wherein this range is modified to account for the amount of time that has already passed since a triggering event has occurred.

In an aspect, a method for operating an implantable cardiac rhythm management device includes detecting a triggering event, starting a preselected first time period to run, wherein the first time period is greater than or equal to 0.5 hours and less than or equal to 24 hours; and executing a post-procedural system check procedure after the expiration of the preselected first time period. The post-procedural system check procedure can include measuring diagnostic properties for one or more of a plurality of electrodes of an electrical stimulation lead attached to the implantable cardiac rhythm management device.

In addition, or alternatively, the triggering event can include an implant-related event.

In addition, or alternatively, the implant-related event such as connection of the electrical stimulation lead to the implantable cardiac rhythm management device and/or exiting of the implantable cardiac rhythm management device out of a storage mode.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope herein is defined by the appended claims and their legal equivalents.

BRIEF DESCRIPTION OF THE FIGURES

Various aspects may be more completely understood in connection with the following drawings, in which.

Figure 1:
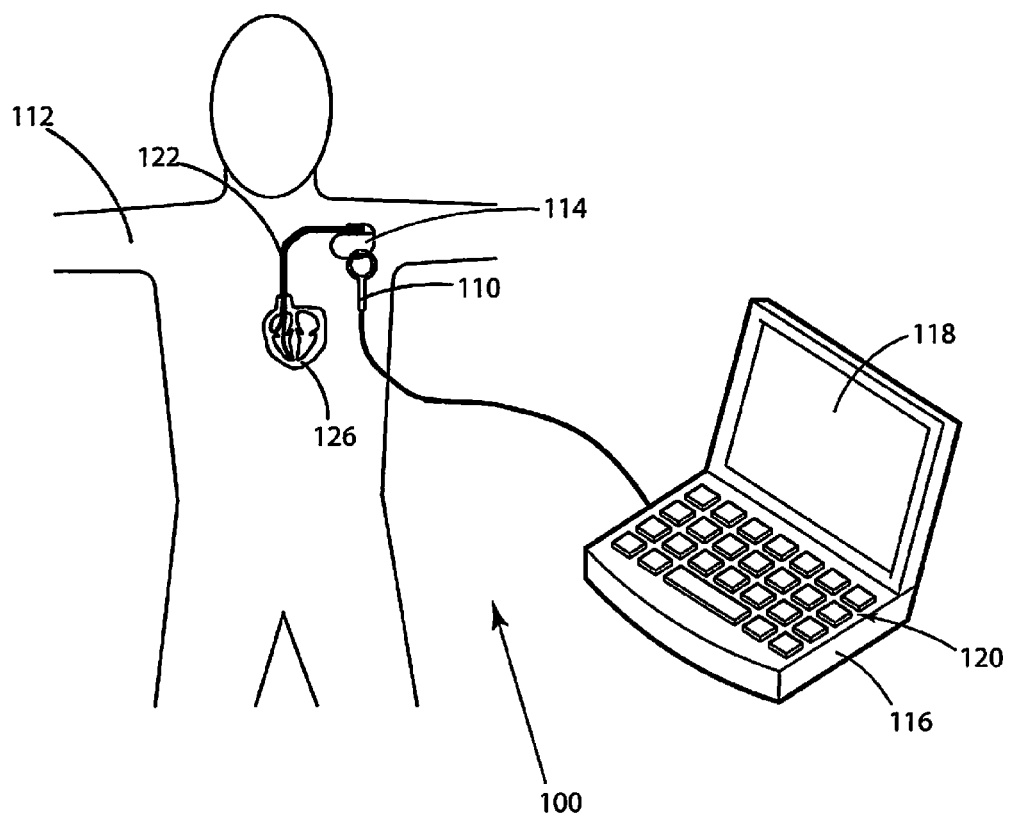
FIG. 1 is a schematic diagram of an exemplary implementation, consistent with various aspects herein.

While aspects herein are susceptible to various modifications and alternative forms, specifics thereof have been shown by way of example and drawings, and will be described in detail. It should be understood, however, that the scope is not limited to the particular embodiments described. On the contrary, the intention is to cover modifications, equivalents, and alternatives falling within the spirit and scope of aspects herein.

DETAILED DESCRIPTION

Aspects described herein are not intended to be exhaustive or to limit the scope to the precise forms disclosed in the following detailed description. Rather, the embodiments are chosen and described so that others skilled in the art can appreciate and understand the principles and practices of the present embodiments.

All publications and patents mentioned herein are hereby incorporated by reference. The publications and patents disclosed herein are provided solely for their disclosure. Nothing herein is to be construed as an admission that the inventors are not entitled to antedate any publication and/or patent, including any publication and/or patent cited herein.

In many treatment scenarios a patient may have a medical device implanted to aid in the functioning of an organ of the body, such as the heart. The implantable medical device can, in turn, be coupled with one or more electrical leads that are also implanted within the patient in order to provide electrical stimulation and/or sensing functions. By way of example, a lead can extend from the implantable medical device to a portion of the patient's heart or near a portion of the patient's heart. However, it will be appreciated that leads can also be implanted in association with other organs as well.

At a time after the procedure of implanting the implantable medical device and the leads, a system check procedure can be conducted to ensure the implantable medical device and the leads are properly implanted and properly working. Results of the system check procedure can be relayed to a system operator, such as through an external medical device.

Various aspects described herein can include a system that can automatically run one or more system tests and, in some aspects, can facilitate providing the results of the system test to an operator. Therefore, because of the automated nature of the testing, the system can provide a more streamlined process for discharging the patient from a healthcare facility after the medical device is implanted or after a different medical procedure.

The system can include an implantable medical device and/or an external medical device. In an embodiment, the implantable medical device can be configured to conduct the system check procedure automatically after a first time period expires. In an embodiment, the implantable medical device can be configured to be ready to report the results of the system check procedure and/or actually report the results at a specified time, such as a time specified by a system operator. In some aspects, the system check procedure can start at a time before the specified time, such that the system check procedure can be completed by the specified time.

The first time period can begin to elapse as a result of various triggers. By way of example, in some embodiments, the first time period can begin to elapse after an implanted device is issued a command to change from a storage mode to an operation mode.

In some embodiments, the first time period can begin to elapse after an implanted device detects the connection of an electrical stimulation lead to a corresponding port on the implanted device. One way this can be accomplished is by the system detecting a change in the impedance of a circuit that is affected by the connection of an electrical stimulation lead to a port on the medical device. For example, the system may evaluate the impedance periodically and if it detects an impedance below a certain threshold, then it concludes that an electrical stimulation lead has been connected.

In some aspects, the implantable medical device can conduct a system check procedure after exposure of the device to conditions associated with a medical procedure. By way of example, the system can conduct a system check procedure after the detection of an MRI to ensure that the MRI did not disrupt or change the desired function of the implantable medical device. In some aspects, the implantable medical device can conduct a system check procedure after detection of specific conditions. By way of example, in some embodiments, the first time period can begin to elapse after detection of an external high voltage shock. In some embodiments, the first time period can begin to elapse after the device detects the invocation of a magnet pacing mode. In some embodiments, a system operator can specifically direct the implantable medical device to conduct a system check procedure, such as through use of the external medical device.

In reference now to the figures, FIG. 1 is a schematic diagram of an exemplary system 100, consistent with various aspects herein. The system 100 can include an implantable medical device 114 disposed within a patient 112. The implantable medical device 114 can be of various types such as, for example, cardiac rhythm management device (including, but not limited to, a pacemaker, a cardioverter-defibrillator, or a cardiac resynchronization device), a neuromodulation device, an implantable monitor, or the like. One example of an implantable medical device is disclosed in commonly assigned U.S. Pat. No. 4,562,841, the content of which is herein incorporated by reference in its entirety. In some embodiments, the implantable medical device 114 can include one or more leads 122 disposed in or near the patient's heart 126.

The implantable medical device 114 can be in communication with an external medical device 116. In some embodiments, communication between the implantable medical device 114 and the external medical device 116 can be via inductive communication through a wand 110 held on the outside of the patient 112 near the implantable medical device 114. However, it will be appreciated that in other embodiments, communication can be carried out via radiofrequency transmission, acoustically, or the like.

The implantable medical device 114 can include one or more implantable sensors in order to gather data regarding the patient 112. Exemplary implantable sensors and types of data are described in greater detail below. In some embodiments, the sensors can be in or on the implantable medical device. In other embodiments, the sensors can be remote from the implantable medical device, but in either wired or wireless communication with the implantable medical device.

The implantable medical device 114 can be configured to store data over a period of time, and periodically communicate with the external medical device 116 in order to transmit some or all of the stored data. In various embodiments, the communication is initiated by the external medical device 116. Such stored data can specifically include the results of system diagnostic tests (or system check procedures) as described herein.

The external medical device 116 can also include a video output device, such as a display screen 118 for displaying video output. In some embodiments, the external medical device 116 can be configured to process the gathered data. The external medical device 116 can also include an operator input device 120, such as a keyboard or other input devices such as a mouse, touchscreen, or the like. In some embodiments, the external medical device 116 can either include or be connected to a printing device. The external medical device 116 can be for example, a programmer/recorder/monitor device, a computer, an advanced patient management system, or a personal digital assistant (PDA). Exemplary programmer/recorder/monitor devices include the Model 3120 Programmer, available from Boston Scientific Corporation, Natick, Mass.

Figure 2:
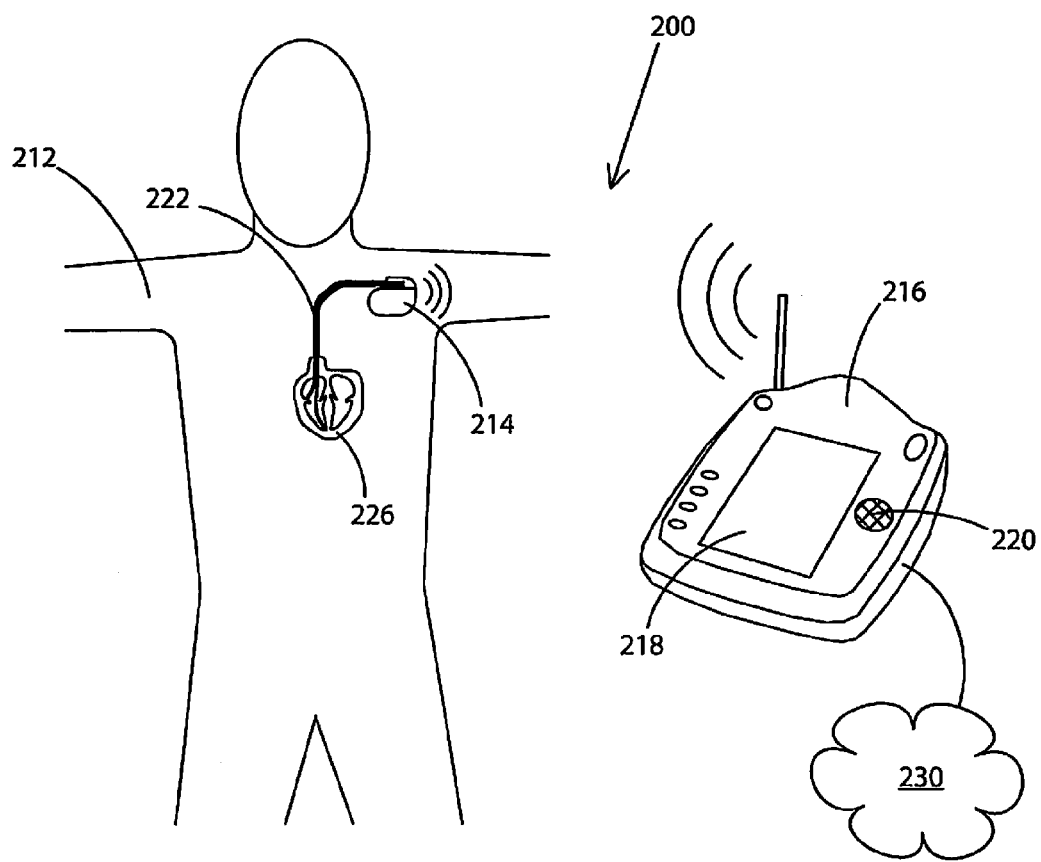
FIG. 2 is a schematic diagram of an exemplary implementation, consistent with various aspects herein.

As an example of a different external device, FIG. 2 is a schematic of another exemplary system 200, consistent with various aspects herein. An implantable medical device 214, implanted within a patient 212, is in communication with an external device 216. Communication between the implantable medical device 214 and the external device 216 can be through radio frequency, inductive transmission, acoustically, or any other means available. In some embodiments, the implantable medical device 214 can include one or more leads 222 disposed in or near the patient's heart 226.

In this example, the external device 216 can be an in-home monitoring system for use by a patient in their home or residence. The external device 216 can have a video output in the form of a display screen 218, and in some cases, an audio output in the form of a speaker 220. An exemplary in-home monitoring system is the LATITUDE® patient management system, available from Boston Scientific Corporation, Natick, Mass. Aspects of exemplary in-home monitoring systems are described in U.S. Pat. No. 6,978,182, the content of which is herein incorporated by reference in its entirety. In such a situation, the external device 216 can be in communication with an additional processing device such as a workstation or server remote from the external device 216 to enable access to the information by doctors or technicians. For example, the external device 216 can be in communication with a workstation or server through the Internet 230 or another type of data connection. In some embodiments, the external device can be a mobile device (not shown), such as a hand-held device or a device worn on a belt.

Figure 3:
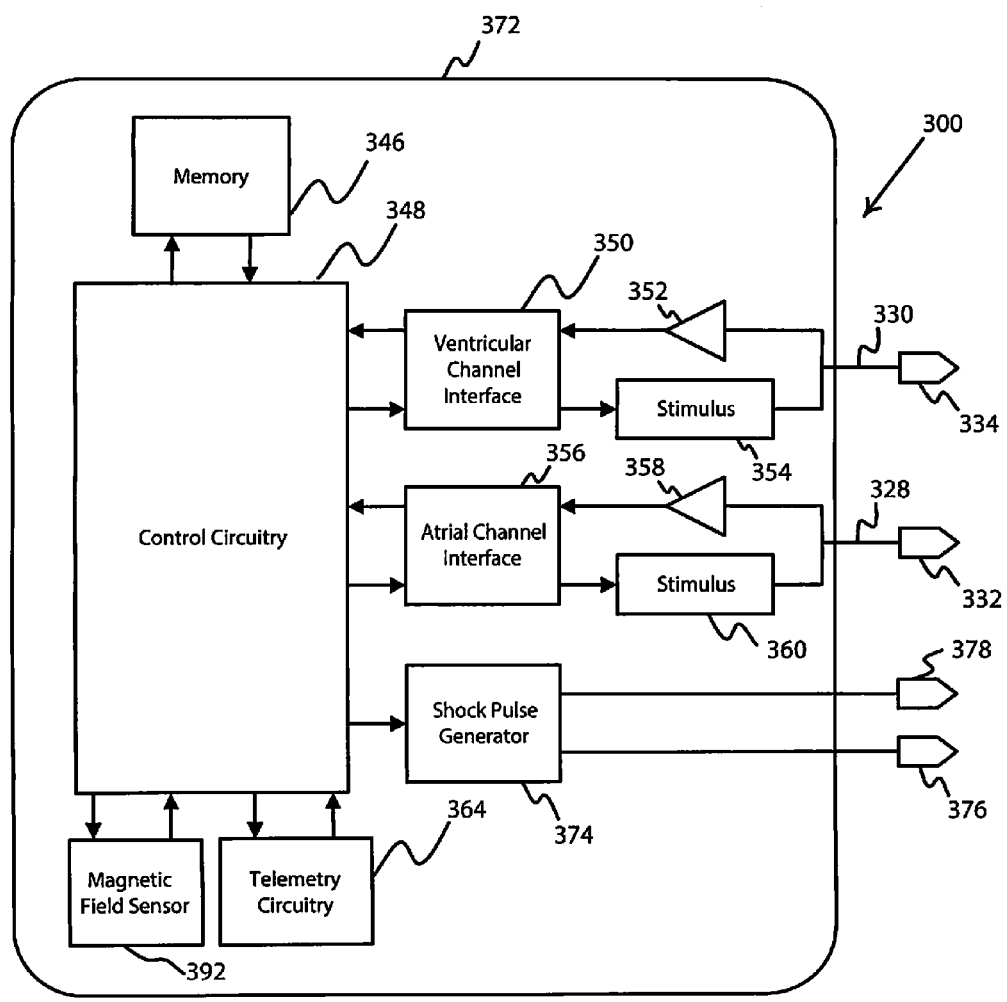
FIG. 3 is a schematic diagram of components of a device, consistent with various aspects herein.

Referring now to FIG. 3, some components of an exemplary implantable system 300 are schematically illustrated. The implantable medical device 300 can include a housing 372 within components therein electrically coupled to one or more stimulation leads 330 and 328. Components inside the housing 372 can include control circuitry 348 (that can include a microprocessor or processor amongst other things) that communicates with a memory 346 via a bidirectional data bus. The memory 346 typically includes ROM or RAM for program storage and RAM for data storage. The control circuitry 348 can be configured to execute various operations such as processing of signals and execution of methods as described herein. Telemetry circuitry 364 is also provided for communicating with an external unit, such as a programmer device or a patient management system. The telemetry circuitry 364 can be in electrical communication with the control circuitry 348.

Components inside the housing 372 can also include ventricular sensing and pacing channels including sensing amplifier 352, output circuit 354, and a ventricular channel interface 350 which communicates bidirectionally with a port of control circuitry 348. It will be appreciated that in some embodiments some of the components inside the housing 372 shown in FIG. 3 may be omitted. Further, in some embodiments, additional elements may be included.

The ventricular sensing and pacing channel can be in communication with stimulation lead 330 and electrode 334. Components inside the housing 372 can include atrial sensing and pacing channels including sensing amplifier 358, output circuit 360, and an atrial channel interface 356 which communicates bidirectionally with a port of control circuitry 348. The atrial sensing and pacing channel can be in communication with stimulation lead 328 and electrode 332. For each channel, the same lead and electrode can be used for both sensing and pacing. The channel interfaces 350 and 356 can include analog-to-digital converters for digitizing sensing signal inputs from the sensing amplifiers and registers which can be written to by a microprocessor in order to output pulses, change the pacing pulse amplitude, and adjust the gain and threshold values for the sensing amplifiers.

In an embodiment, a shock pulse generator 374 can also be interfaced to the control circuitry for delivering defibrillation shocks to the heart via a separate pair of electrodes 376, 378. In some embodiments, electrodes 376 and 378 can be disposed along stimulation lead 330 and stimulation lead 328 respectively. However, it will be appreciated that in some aspects, such as in the case of a pacemaker without cardioversion capabilities, that the shock pulse generator 374 and associated components can be omitted. In some embodiments, other components can be included such as sensors (chemical, optical, gyroscopic, accelerometers, and the like) that can have associated channel interfaces.

The housing 372 can be hermetically sealed. The housing 372 can define a cavity, such as a space for circuitry to be disposed within. Frequently, the housing can be referred to as a "can".

The control circuitry 348 can be configured to execute a post-procedural system check procedure, such as after a first time period. In an embodiment, the first time period can be preselected, such that the first time period is selected prior to the implantable medical device being implanted or prior to a triggering event. The post-procedural system check procedure can be conducted after a procedure. In this context, the term post-procedural can refer to being after a medical procedure. Exemplary medical procedures can including diagnostic procedures (including x-rays, MRIs, CT scans, and the like), therapeutic interventions, procedures directly related to the implantable system (such as implanting of the device, and procedures that are not directly related to the implantable system). As such, in some embodiments, the system check procedure can take place after the procedure to implant the implantable medical device in the patient. In an embodiment, the post-procedural system check can be a post-operative system check, such as when the system check occurs after an operation. The system check procedure can be a procedure in which one or more aspects of the system are checked, evaluated, or otherwise tested to determine if the one or more aspects are in the desired condition for use on the patient.

The first time period can be a period of time that starts when a triggering event is detected or a command by a system operator is detected. A triggering event can include an implant related event, such as an event that occurs in accordance with the implantable medical device being implanted into the patient. Examples of implant related events can include connection of an electrical stimulation lead to the implantable medical device, or the implantable medical device exiting out of a storage mode. The storage mode can be consistent with a mode the implantable medical device is in when it is not in use, such as in storage prior to being implanted. A triggering event can include the detection of an MRI time varying magnetic field, such as if the patient has an MRI. It will be appreciated that detecting of an MRI magnetic field can be accomplished in various ways such evaluating the output from a sensor (such as magnetic field sensor 392 in FIG. 3), such as a magnetic field gradient sensor, a magnetometer, a Hall-effect sensor, or a reed switch that is configured to enable detection of the strong magnetic field associated with MRI.

A triggering event can include the initiation of a magnet pacing mode. Magnet pacing is typically nominally an asynchronous pacing mode at a particular rate (e.g., from 120-70 ppm) that is initiated as a result of the detection of a magnetic field such as would be caused by the placement of a magnet near the implantable device. A magnet pacing mode can be used to provide asynchronous packing support and enable clinicians to assess various aspects of the implanted device without using a programmer device. In many cases, operational aspects of a magnet pacing mode can be configured by a system user.

In an embodiment, the first time period can begin to elapse after a command by a system operator is detected. A system operator or user can send a command to the implantable medical device to start the first period of time, such as if the system operator wants to implantable medical device to execute a post-procedural system check to ensure the implantable medical device is in acceptable condition.

In an embodiment, the first time period can be at least 0.5 hours long and not more than 48 hours long. In an embodiment, the first time period can be at least 2 hours long and not more than 24 hours long. The first time period can have a default length of time that is stored by the control circuitry, prior to the device exiting the storage mode. The default length of time can be preset, such as during manufacturing of the implantable medical device. In an embodiment, a system operator can specify or input a first time period, such as through the external medical device.

The control circuitry can be configured to send an indication of the current status and/or data from the post-procedural system check if the implantable medical device is interrogated during or after the post-procedural system check. In an embodiment, a system operator can interrogate or otherwise prompt the implantable medical device for information (current status, results, data, etc. . . . ) from the post-procedural system check, such as through an external medical device. If a post-procedural system check is currently being conducted when the system operator interrogates the implantable medical device, the control circuitry can send information regarding the current status of the post-procedural system check or data from the check in progress.

The control circuitry can be configured to report the results from the post-procedural system check, such as via the telemetry circuitry to an external device. The control circuitry can report the results at the termination of the post-procedural system check or at the next communication request, such as a request initiated by a system operator and/or an external device.

In some aspects, the control circuitry can be configured to accept input from a system operator specifying a desired time for the post-procedural system check procedure to start or for the results of the post-procedural system check to be available. The control circuitry can calculate the length of the first time period based on the input from the system operator. In some aspects, the calculated length of the first time period can be less than the amount of time specified by the operator. In an embodiment, the system operator can use an external device to transmit the input to the control circuitry within the implantable medical device.

In an embodiment, the system operator can specify a time in which the system operator wants the results of the post-procedural system check. The control circuitry can be configured to calculate the time the post-procedural system check needs to start to have the results ready by the specified time.

For example, at 6:00 AM the system operator can request the results be ready at 12:00 PM. If the control circuitry has information that the system check will take 30 minutes, the system check would start no later than 11:30 AM, and therefore the first time period can be set at 5.5 hours in this example.

The post-procedural system check procedure can include measuring diagnostic properties for one of more of the electrodes of an electrical stimulation lead attached to the implantable medical device. The diagnostic properties can include at least one of an impedance test, an intrinsic amplitude test, and a pacing threshold test.

The impedance test can include measuring impedance (Ohms) for a particular set or sets of electrodes (e.g., tip to can, tip to ring, ring to can, etc.) for leads corresponding to various chambers of the heart. Impedance measurements can be used to aid in determining whether the leads are functioning properly. By way of example, impedance testing results can be used as a relative measure of lead integrity over time. In some aspects, impedance can be measured in various ways including approaches based on the relationship between voltage, current and resistance described by Ohm's Law (V=IR) with or without the effects of capacitance and inductance. In some aspects, for a pace/sense lead impedance test, the implanted device can function in a triggered pacing mode at a particular amplitude (e.g., including but not limited to 5.0 V or 7.5 V) at a particular pulse width. In various aspects, for a pace/sense lead impedance test, the implanted device can deliver a subthreshold energy pulse through a set or sets of the pace/sense electrodes. For a shock lead impedance test, the implanted device can deliver a subthreshold energy pulse through the shocking electrodes.

The intrinsic amplitude test can include measuring intrinsic (versus evoked) P and R wave amplitudes for the respective chambers of the heart. It will be appreciated that there are various ways of measuring intrinsic amplitude. By way of example, the amplitude (for example, in mV) of intrinsic P and R waves can be measured using a particular set or sets of electrodes and determining the difference in electrical potential. The measured intrinsic amplitude can be specific to a particular chamber of the heart through the selection of particular electrodes corresponding thereto.

The pacing threshold test (or capture threshold test) can include determining the threshold for capture and induction of an evoked contraction. Pacing thresholds can be checked to ensure reliable pacing. Significant changes in pacing thresholds can be caused by various conditions but frequently merit follow-up by a clinician. In addition, capture detection can allow the device to adjust the energy level of pacing pulses to correspond to the optimum energy expenditure that reliably produces a contraction. It will be appreciated that there are various approaches for executing a pacing threshold test. In general, parameters of the pacing pulses can be varied in terms of amplitude (in some cases other parameters can also be varied such as pulse width) and the system then attempts to sense evoked responses. When evoked responses are no longer detected, thresholds can be determined. Many specific approaches exist, including those described in U.S. Pat. No. 8,725,261, the content of which is herein incorporated by reference. Another approach is described in U.S. Pat. No. 8,060,205, the content of which is herein incorporated by reference.

In an embodiment, an external medical device can be provided. The external medical device can allow a system operator to review results of a post-procedural system check procedure, or request a post-procedural system check to be performed. The external medical device can be in wireless communication with the implantable medical device, such as to receive results from a system check or to request a system check be performed.

The external medical device can include a housing, control circuitry disposed within the housing, telemetry circuitry in electrical communication with the control circuitry, a display device operatively coupled to the housing, and an operator input device operatively coupled to the housing.

In an embodiment, the external device can be located in the proximity of the patient, such as within or near a patient's place of residence. Additionally, the external device can be located remote from a care provider, such as not within the same building as the care provider.

The control circuitry of the external device can be configured to display information through the display device regarding the results of a previously executed post-procedural system check procedure. The control circuitry can be configured to display information through the display device information the operator of the external device that a post-procedure system check is in process, if execution of an attempted post-procedural system check procedure has not terminated. In some embodiments, the control circuitry of the external medical device can be configured to print information regarding the results of a previously executed post-procedural system check procedure through an integrated or separate printing device.

In an embodiment, the control circuitry of the external medical device can be configured to display one or more fields regarding recent system check results, such as measured impedance values. The fields can be populated with information from a previously executed post-procedural system check or an automatic daily lead test. In an embodiment, the fields are populated with the more recent of a previously executed post-procedural system check and an automatic daily lead test.

The control circuitry of the external medical device can be configured to accept input from a system operator, such as through the operator input device. The operator can input information regarding a desired time for the post-procedure system check, such as when the operator wants the post-procedure system check completed by. The external medical device can display information to the system operator through the display device regarding an acceptable range of the operator input. In some aspects, the range can be modified to account for the amount of time that has already passed since a triggering event has occurred.

Figure 4:
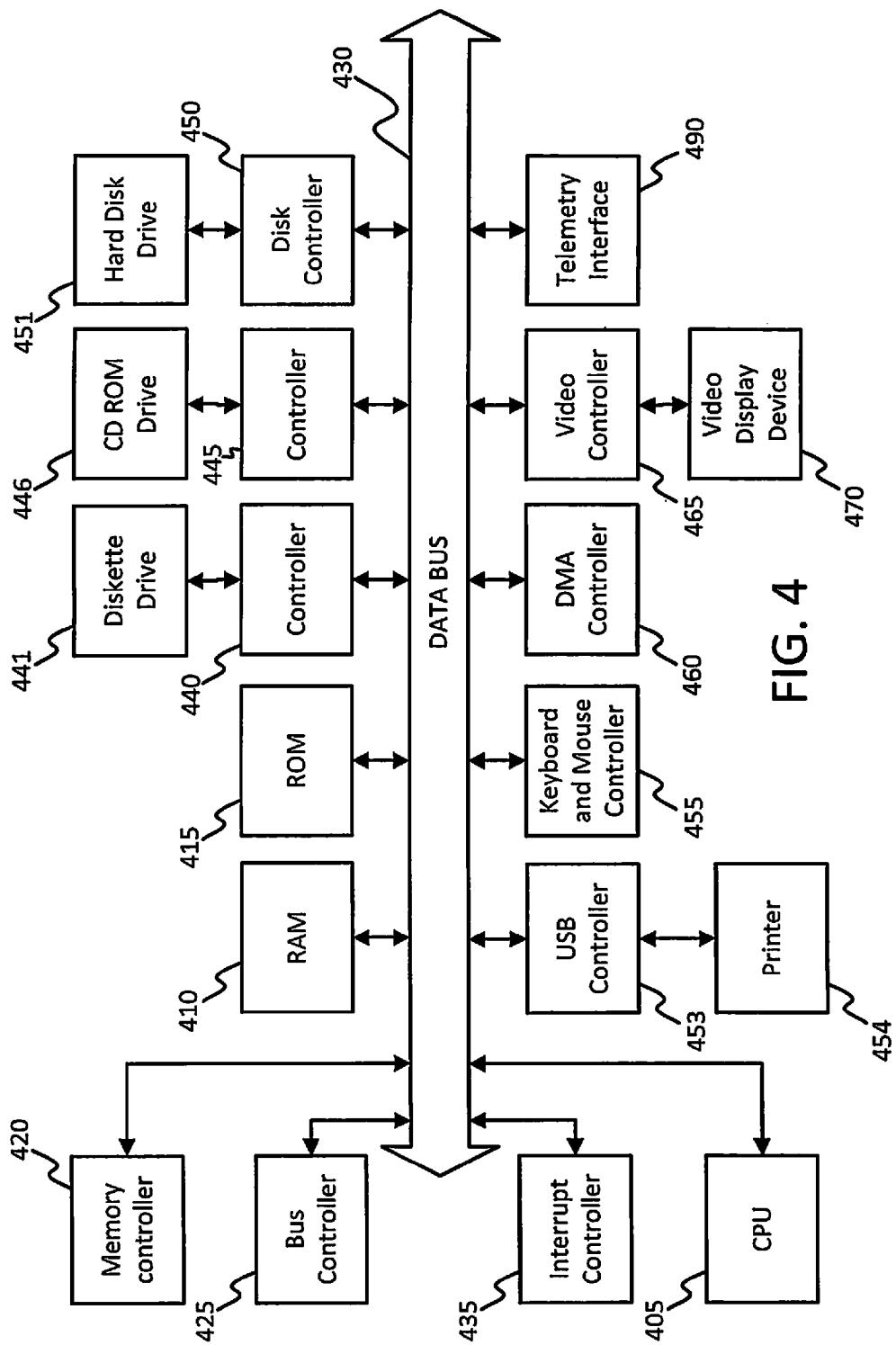
FIG. 4 is a schematic diagram of various programmer/recorder/monitor components, consistent with various aspects herein.

External devices, such as external medical devices/programmer/recorder/monitors, can include components common to many computing devices. Referring now to FIG. 4, a diagram of various components is shown consistent with various aspects herein. The external system includes a central processing unit (CPU) 405 or processor, which may include a conventional microprocessor, random access memory (RAM) 410 for temporary storage of information, and read only memory (ROM) 415 for permanent storage of information. A memory controller 420 is provided for controlling system RAM 410. A bus controller 425 is provided for controlling data bus 430, and an interrupt controller 435 is used for receiving and processing various interrupt signals from the other system components. These components can be referred to as control circuitry.

Mass storage can be provided by diskette drive 441, which is connected to bus 430 by controller 440, CD-ROM drive 446, which is connected to bus 430 by controller 445, and hard disk drive 451, which is connected to bus 430 by controller 450. Operator input to the programmer system may be provided by a number of devices. For example, a keyboard and mouse can be connected to bus 430 by keyboard and mouse controller 455. DMA controller 460 is provided for performing direct memory access to system RAM 410. A visual display is generated by a video controller 465 or video output, which controls video display 470. The external system can also include a telemetry interface 490 or telemetry circuit which allows the external system to interface and exchange data with an implantable medical device. The system can also include an interface such as a USB controller 453. The USB controller 453 can be connected to various other devices. In some embodiments, a printer 454 or similar physical output unit can be connected to the USB controller 453 or through a similar interface. The printer can either be integrated with other components herein or can be separate. It will be appreciated that some embodiments may lack various elements illustrated in FIG. 4.

Figure 5:
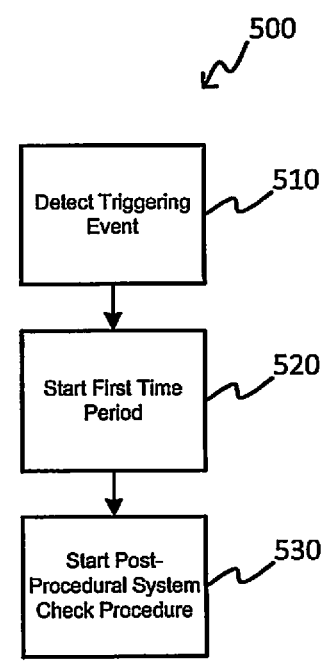
FIG. 5 is a flow chart depicting a method for operating an implantable medical device, consistent with various aspects herein.

Devices and control circuitry thereof can be configured to execute various operations herein. In particular, devices and control circuitry thereof can be configured to execute operations associated with methods herein. FIG. 5 shows a flow chart depicting a method of operating an implantable medical device, consistent with various aspects herein. In an embodiment, the method 500 can include detecting a triggering event 510. As discussed above, the triggering event can include an implant-related event, such as connecting an electrical stimulation lead to the implantable medical device or exiting the implantable medical device out of a storage mode.

The method can also include starting a first time period to run 520, such as a preselected first time period. The first time period can be greater than or equal to 0.5 hours and less than or equal to 24 hours.

The method can also include executing a post-procedural system check procedure after the expiration of the first time period 530. The post-procedural system check procedure can include measuring diagnostic properties for one or more of a plurality of electrodes of an electrical stimulation lead attached to the implantable medical device. In an embodiment, the post-procedural system check can include one or more of the following: an impedance test, an intrinsic amplitude test, or a pacing threshold test.

The method can also include presenting the results of the system check procedure to a system operator, such as through an external medical device. The system operator can review the results from the system check procedure, such as to determine if the implantable medical device is in the desired configuration or operating properly.

Figure 6:
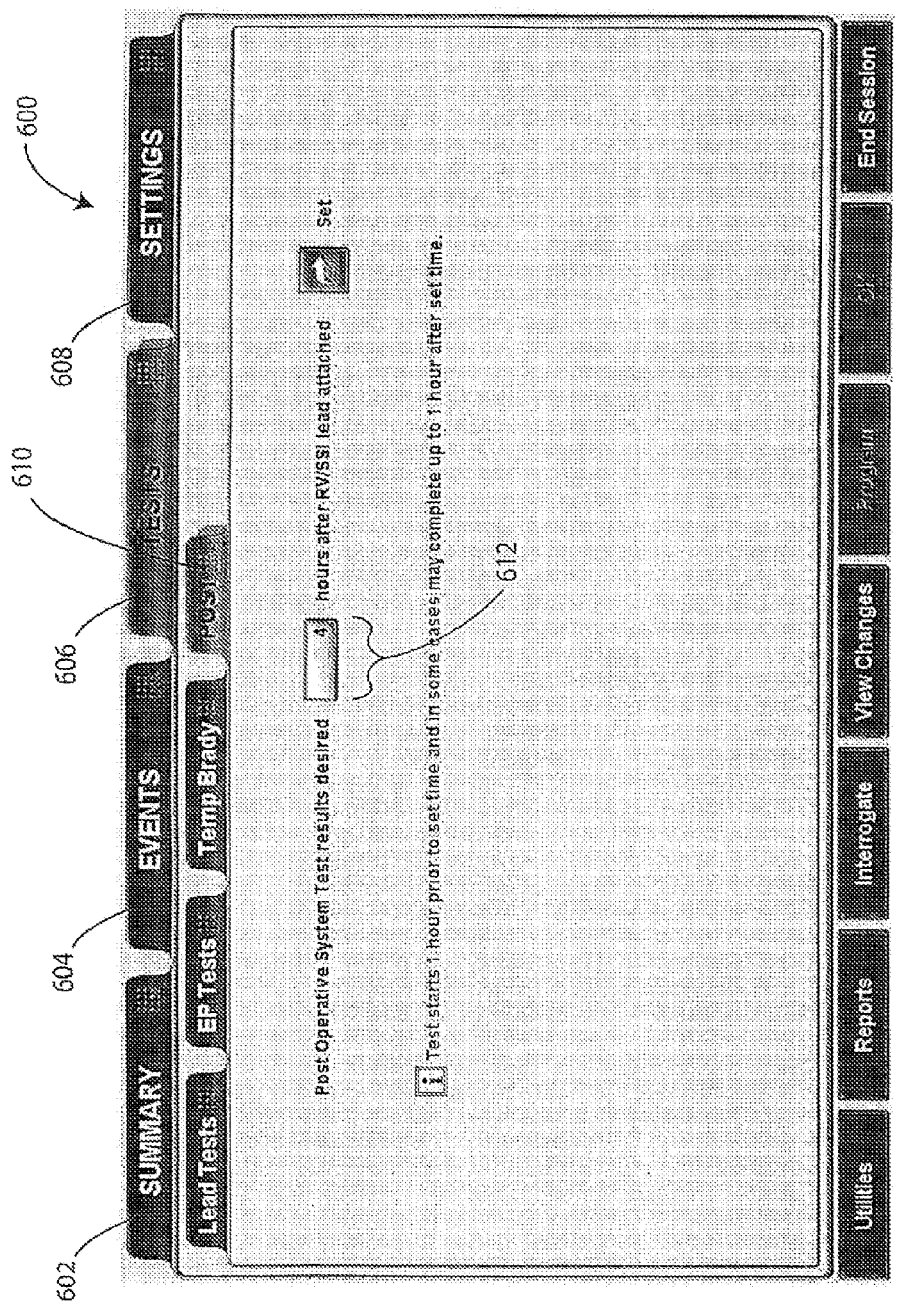
FIG. 6 is a schematic view of a portion of a user interface, consistent with various aspects herein.

FIG. 6 is a schematic view of a portion of a user interface 600, consistent with various aspects herein. External devices herein can be configured to display the user interface 600 to a system operator or user. The user interface 600 can allow the operator to enter commands for the implanted medical device, such as to schedule a system check procedure, and/or review results from a previously completed system check procedure, and/or to receive a status update for a current system check procedure. In some embodiments, as shown in FIG. 6, the user interface 600 can include multiple tabs that include different information, such as a "SUMMARY" tab 602 to display a summary of information, an "EVENTS" tab 604 to show scheduled (past or future) tests, and a "SETTINGS" tab 608 to allow an operator to change or modify different settings for the implantable medical device or the external medical device. A "TESTS" tab 606 can include various sub-tabs and, in particular, a "POST" sub-tab 610 under the "TESTS" tab 606 can display information including parameters of a post-procedural system check procedure and specifically allow a user to input a desired time 612 when post-procedural system check procedure result should be available specified either as an absolute time or as a number of hours from a particular event or trigger. It will be appreciated that in various embodiments external devices can be configured to print the same or similar information to that shown in FIG. 6, whether the information is shown through a user interface or not.

Figure 7:
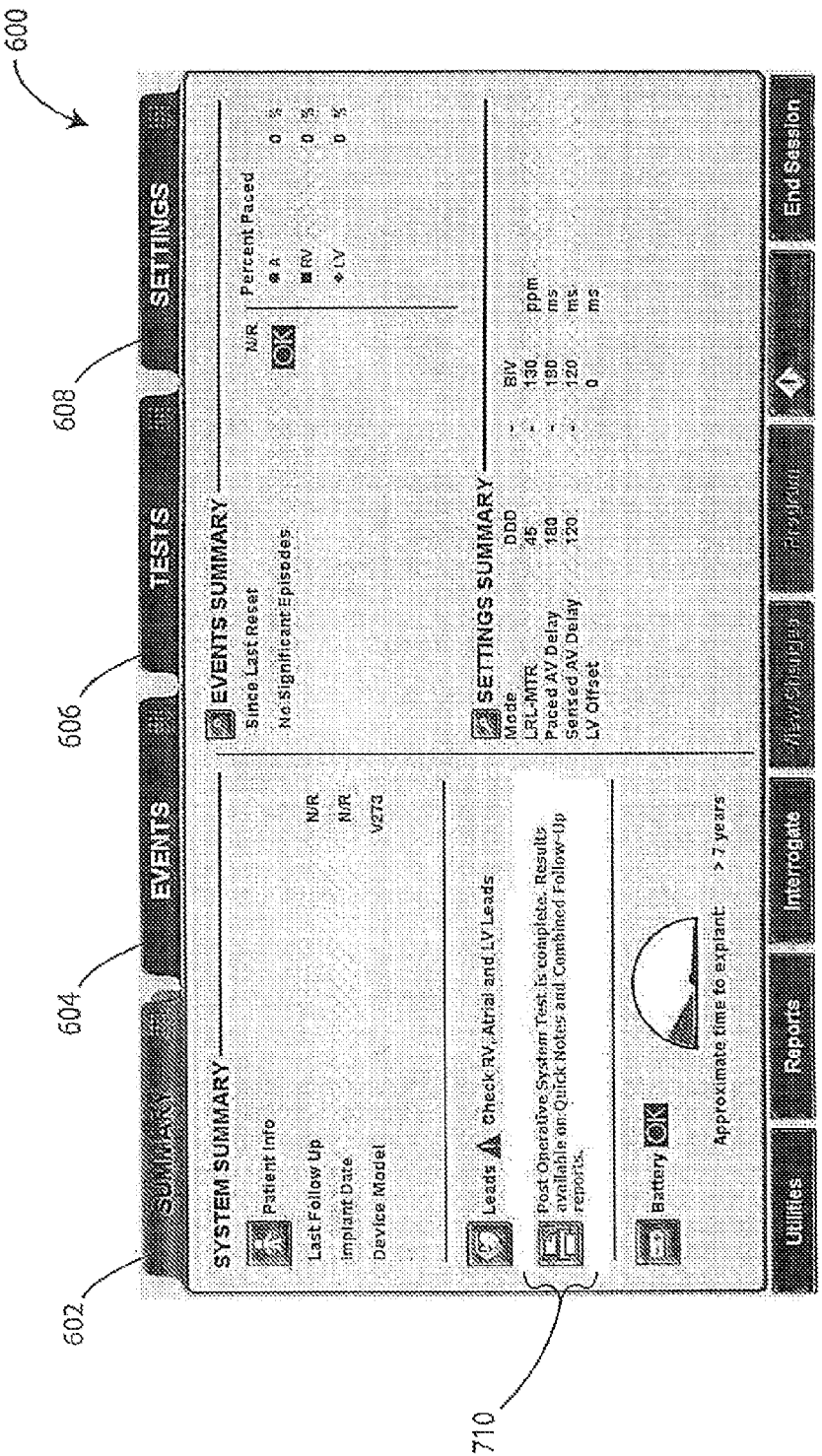
FIG. 7 is a schematic view of a portion of a user interface, consistent with various aspects herein.

FIG. 7 is a schematic view of the "SUMMARY" tab 602 of the user interface, consistent with various aspects herein. The "SUMMARY" tab 602 can show the operator a general overview of information, such as patient information, lead information, battery information, event information, and setting information. The "SUMMARY" tab 602 can display warnings to the operator, such as a warning that an unexpected result was found during a system check procedure. In particular, the "SUMMARY" tab 602 can display information regarding a post-procedural system check procedure 710 including, but not limited to, the status thereof. It will be appreciated that in various embodiments external devices can be configured to print the same or similar information to that shown in FIG. 7, whether the information is shown through a user interface or not.

Figure 8:
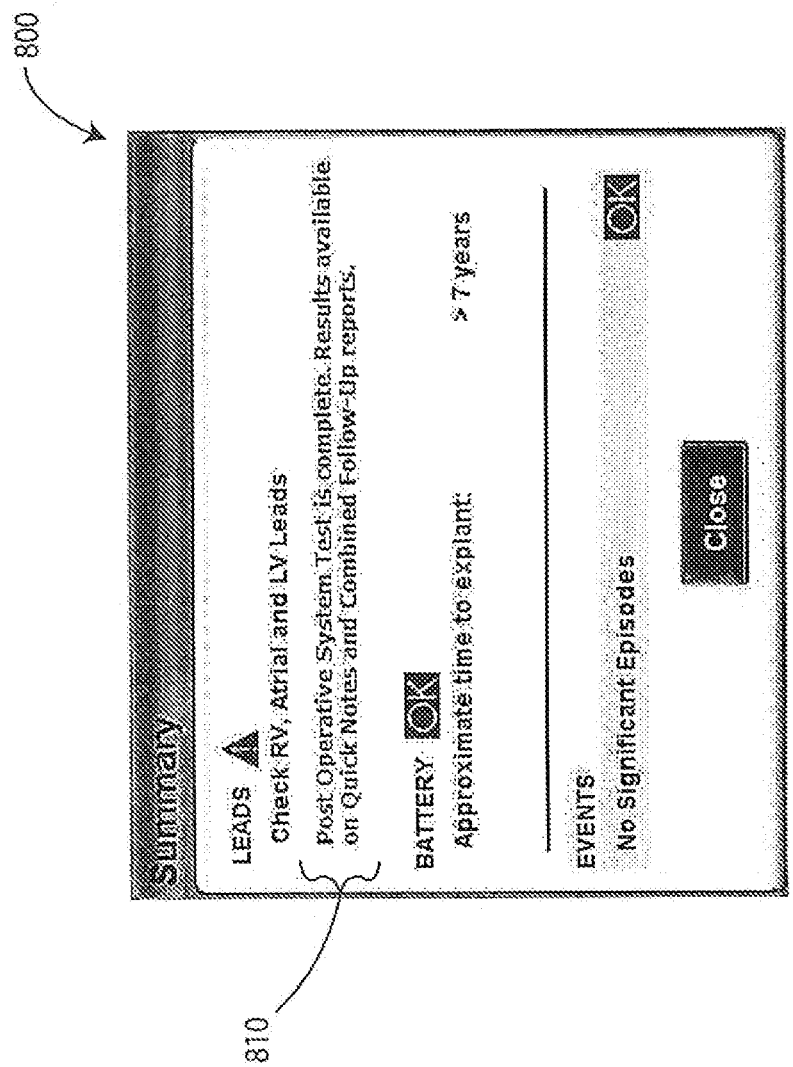
FIG. 8 is a schematic view of a portion of a user interface, consistent with various aspects herein.

FIG. 8 is a schematic view of a pop-up "SUMMARY" box 800 as part of a user interface in accordance with various aspects herein, which can appear in addition to, or alternatively, with regard to other user interface elements described herein. Amongst other pieces of information, the pop-up box 800 can display information regarding a post-procedural system check procedure 810 including, but not limited to, the status thereof. It will be appreciated that in various embodiments external devices can be configured to print the same or similar information to that shown in FIG. 8, whether the information is shown through a user interface or not.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration to. The phrase "configured" can be used interchangeably with other similar phrases such as arranged and configured, constructed and arranged, constructed, manufactured and arranged, and the like.

All publications and patent applications in this specification are indicative of the level of ordinary skill in the art to which aspects herein pertain. All publications and patent applications are herein incorporated by reference to the same extent as if each individual publication or patent application was specifically and individually indicated by reference.

Aspects herein have been described with reference to various specific and preferred embodiments and techniques. However, it should be understood that many variations and modifications may be made while remaining within the spirit and scope herein.

The invention claimed is:

1. An implantable cardiac rhythm management device comprising a housing;

control circuitry disposed within the housing;

telemetry circuitry in electrical communication with the control circuitry; and a magnetic field sensor in electrical communication with the control circuitry;

wherein the control circuitry is configured to execute a post-procedural system check procedure after a expiration of a preselected first time period, wherein the first time period is longer than 0.5 hours and less than 48 hours;

the post-procedural system check procedure comprising measuring diagnostic properties for one or more of a plurality of electrodes of an electrical stimulation lead attached to the implantable cardiac rhythm management device;

wherein the first time period begins to elapse based on detection of a triggering event by the magnetic field sensor.

2. The implantable cardiac rhythm management device of claim 1, the triggering event comprising detecting an MRI time varying magnetic field.

3. The implantable cardiac rhythm management device of claim 1, the triggering event comprising initiation of a magnet pacing mode.

4. The implantable cardiac rhythm management device of claim 1, the diagnostic properties comprising at least one selected from the group consisting of an impedance test, an intrinsic amplitude test, and a pacing threshold test.

5. The implantable cardiac rhythm management device of claim 1, wherein the control circuitry is configured to send an indication of a current status and/or data from the post-procedural system check if the implantable cardiac rhythm management device is interrogated during the post-procedural system check.

6. The implantable cardiac rhythm management device of claim 1, wherein the control circuitry is configured to report results of the post-procedural system check procedure via the telemetry circuitry to an external device at a next communication request.

7. The implantable cardiac rhythm management device of claim 6, wherein the external device is in a proximity of the patient in which the implantable cardiac rhythm management device is implanted, but is remote from a care provider.

8. The implantable cardiac rhythm management device of claim 1, wherein the first time period is greater than or equal to 2 hours and less than or equal to 24 hours.

9. The implantable cardiac rhythm management device of claim 1, wherein a default length of the first time period is stored by the control circuitry prior to the device exiting a storage mode.

10. The implantable cardiac rhythm management device of claim 1, the triggering event comprising initiation of an asynchronous pacing mode at a particular rate of 120-70 ppm.

* * * * *